United States Patent [19]

Townsend

[11] 3,998,806

[45] Dec. 21, 1976

[54] α- AND β-2'-DEOXY-6-R-SUBSTITUTED SELENOGUANOSINE COMPOUNDS

[75] Inventor: Leroy B. Townsend, Salt Lake City, Utah

[73] Assignee: The United States of America as represented by the Department of Health, Education and Welfare, Washington, D.C.

[22] Filed: Feb. 26, 1975

[21] Appl. No.: 553,079

[52] U.S. Cl. .................................. 536/24; 424/180
[51] Int. Cl.$^2$ ........................................ C07H 19/16
[58] Field of Search ............................ 260/211.5 R

[56] References Cited
OTHER PUBLICATIONS

Milne et al., "Jour. of Medicinal Chem.", 17, 1974, pp. 263–268.
Chu, "Chem. Abst.", vol. 74, 1971, p. 112375K.
Milne, "Biochem. Biophys. Acta", vol. 269, 1972, pp. 344–346.

Primary Examiner—Johnnie R. Brown
Attorney, Agent, or Firm—John S. Roberts, Jr.; Norman J. Latker; Thomas G. Ferris

[57] ABSTRACT

Treatment of the α and β anomers of 2'-deoxy-6-selenoguanosine with alkyl halides, p-nitrobenzyl bromide, and 5-chloro-1-methyl-4-nitroimidazole under basic conditions has produced the desired products, which are 2'-deoxy-6-R-selenoguanosines where R is the substituent group [2-amino-6-R-seleno-9-(2-deoxy-α- and β-D-erythro-pentofuranosyl)purines] and R is preferably lower alkyl or aryl. The animal test screening indicated substantial activity for several members of this group of compounds against mouse leukemia L-1210.

8 Claims, No Drawings

α- AND β-2'-DEOXY-6-R-SUBSTITUTED SELENOGUANOSINE COMPOUNDS

The present invention relates to the conversion of the α and β anomers of 2'-deoxy-6-selenoguanosine, as, for example, by treatment with alkyl halides under basic conditions to form the corresponding 2'-deoxy-6-alkyl-selenoguanosines or broadly 2'-deoxy-6-R-selenoguanosines [2-amino-6-R-seleno-9-(2-deoxy-α- and β-D-erythro pentofuranosyl)purines]. The R substitutent is selected preferably from lower alkyl and aryl, such as nitrobenzyl and 2-pyridyl methyl as is set out in the pictorial representations below for the anomers.

Chart I

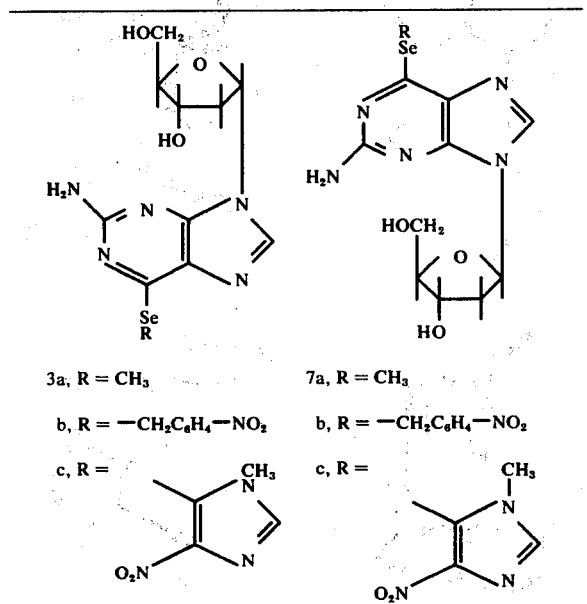

With reference to 3a and 7a in Chart I above, other compounds corresponding to the following R substituents have shown activity: iso-$C_3H_7$, iso-$C_4H_9$, n-$C_3H_7$, benzyl, 2-pyridylmethyl, etc. Selected members of this group of compounds have demonstrated very good anti-leukemia activity in mice against L-1210.

Historically, the interest in the present compounds stems from the known anti-tumor activity of 6-thioguanine (6 TG) which is believed to be active through incorporation into DNA. This activity on further investigation was lessened in several tumor cell lines due to the development towards resistance of chemotherapeutic effect of 6-thioguanine. It was found that the β-2'-deoxythioguanoisine can be phosphorylated with subsequent incorporation into DNA which effectively circumvents the resistant mechanisms observed to develop toward the use of 6-thioguanine. A better therapeutic index with less toxicity and comparable anti-tumor inhibition has been reported for 6-selenoguanine and from this point a synthesis of the α- and β-2'-deoxyribofuranosyl derivatives of 6-selenoguanine was made.

CHART II

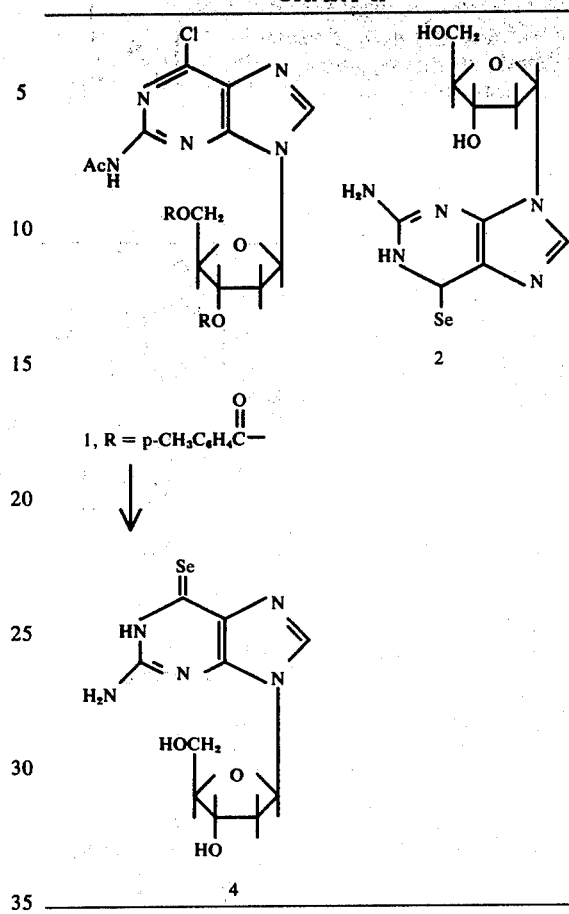

The preparation of the starting materials 4 and 2 above has been described by Milne and Townsend, *Biochem. Biophys. Acta*, 269 (1972) 344–346, entitled "The Synthesis of α- and β-2'-Deoxyselenoguanosine." In the above, the treatment of 2-acetamido-6-chloro-9-(2-deoxy-3-5-di-0-p-toluoyl-β-D-erythro-pentofuranosyl)purine with sodium hydrogen selenide in methanol at reflux temperature for 1 hour under a nitrogen atmosphere effected a nucleophilic displacement of the 6-chloro group as evidenced by thin-layer chromatography (tlc) and ultraviolet (uv) spectrum. The protecting groups were then removed and the respective α and β anomers were recovered and identified as β-2'-deoxy-6-selenoguanosine (4) and α-2'-deoxy-6-selenoguanosine (2).

GENERALIZED PROCESS

With reference to Chart II (ante) and Chart III (below), treatment of 1 with sodium hydrogen selenide in methanol effected a nucleophilic displacement of the 6-chloro group as evidenced by tlc and uv spectrum. The protecting groups were then removed with sodium methoxide in methanol at reflux temperature to furnish a bright yellow crystalline nucleoside which was characterized as β-2'-deoxy-6-selenoguanosine (4).

A similar procedure using 5 furnished a 46% yield of α-2'-deoxy-6-selenoguanosine (2).

The synthesis of both anomers (α and β) of 2'-deoxy-6-selenoguanosine is of interest in view of the reported phosphorylation of both anomers of 2'-deoxy-6-thioguanosine. The α anomer was negative as to activity of phosphorylation in normal tissues studied.

Compound 4 above is alkylated and specifically is methylated with methyl iodide in methanolic sodium methoxide furnishing 2-amino-6-methylseleno-9-(2-deoxy-β-D-erythropentofuranosyl)purine (7a). Methylation or alkylation of 2 gave similar results for the other anomer as product (3a).

CHART III

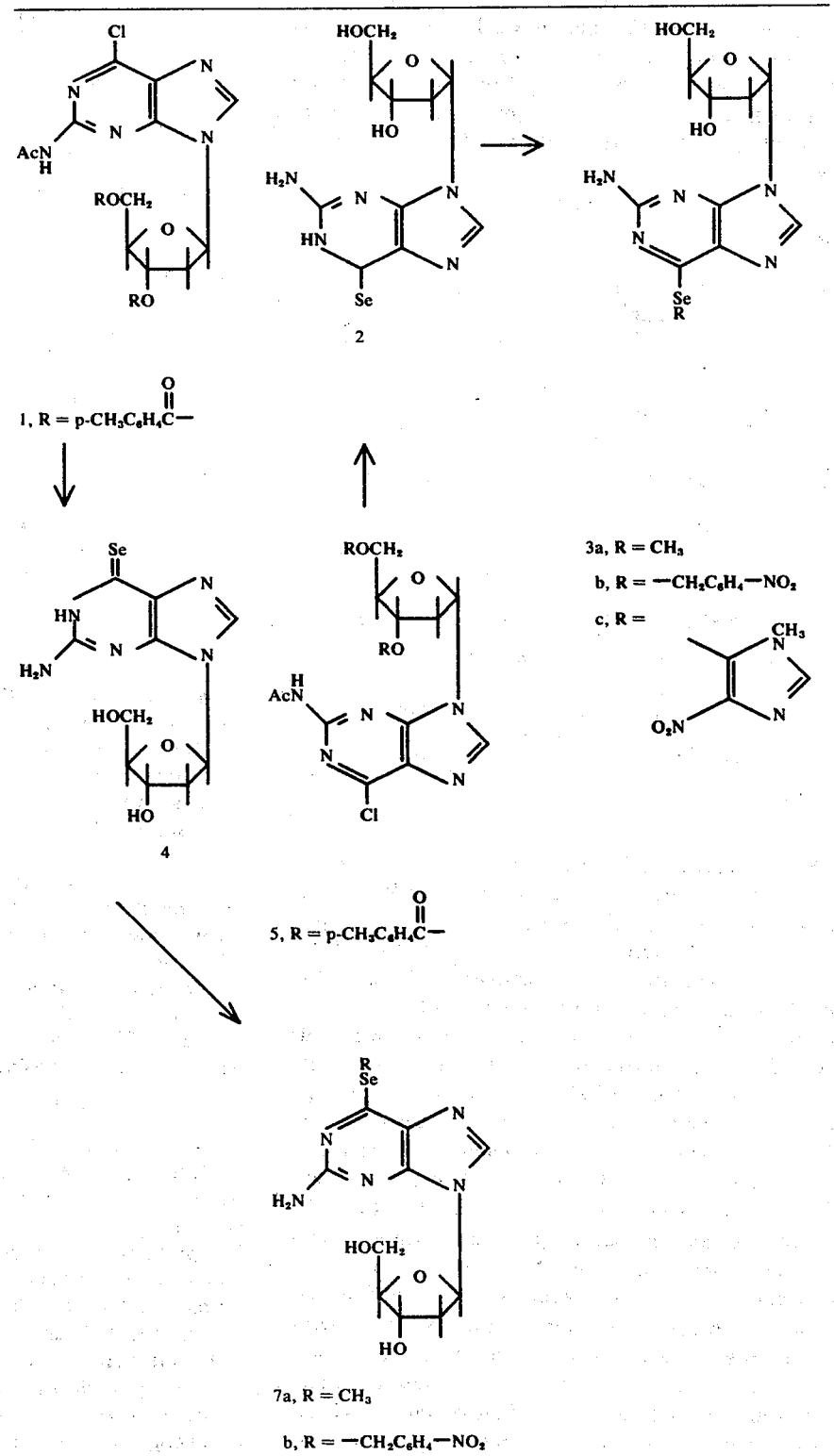

CHART III-continued

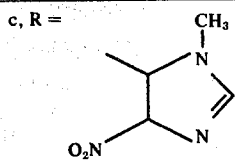

Treatment of 4 with p-nitrobenzyl bromide in methanolic sodium methoxide furnished a good yield of 7b. Similarly. akkylation of 2 with p-nitrobenzyl bromide under similar conditions furnished 3b.

Treatment of 4 and 2 with 5-chloro-1-methyl-4-nitroimidazole under basic conditions in methanol furnished 7c and 3c. respectively.

tant may be utilized in special cases to drive the reaction to the right and effect completion thereof.

Generally speaking, the alkylation of the selenium substituent at the 6 position is achieved in 2 or 4 by alkylating as with lower alkyl halide such as methyl iodide and using methanolic sodium methoxide as the reaction milieu under alkaline pH conditions.

TABLE I

| R | | Dose mg/kg | Survivors | Animal wt diff (T − C) | Survival days T/C | % |
|---|---|---|---|---|---|---|
| H | (α) | 200 | 5/7 | −3.8 | 13.4/9.8 | 136 |
| H | (β) | 200 | 0/7 | −1.4 | 0.0/9.8 | |
| | | 100 | 6/7 | −4.7 | 8.1/9.8 | |
| | | 50 | 6/6 | −3.3 | 11.6/9.4 | 123 |
| | | 25 | 6/6 | −1.6 | 14.1/9.4 | 150 |
| | | 12.5 | 6/6 | −1.9 | 12.8/9.4 | 136 |
| | | 25 | 6/6 | −1.6 | 14.1/9.3 | 151 |
| | | 12.5 | 5/6 | −1.6 | 13.7/9.3 | 147 |
| | | 50 | 6/6 | −2.0 | 15.3/10.2 | 150 |
| | | 25 | 6/6 | −1.1 | 17.5/10.2 | 171 |
| | | 12.5 | 5/6 | .6 | 20.0/10.2 | 196 |
| O₂N-imidazole-CH₃ | (α) | 100 | 6/6 | −1.7 | 11.0/11.2 | 98 |
| | | 50 | 6/6 | −1.1 | 9.2/9.3 | 98 |
| O₂N-imidazole-CH₃ | (β) | 200 | 1/6 | −6.4 | 7.0/11.2 | Toxic |
| | | 100 | 3/6 | −5.4 | 9.3/11.2 | Toxic |
| | | 50 | 3/6 | −2.1 | 13.0/9.3 | |
| | | 25 | 5/6 | −1.9 | 13.4/9.3 | 144 |
| | | 37.5 | 5/6 | − .2 | 28.0/12.1 | 231 |
| | | 25 | 6/6 | 1.2 | 26.8/12.1 | 221 |
| | | 16.5 | 6/6 | 1.7 | 19.3/12.1 | 159 |
| | | 62.5 | 4/6 | −3.1 | 9.8/9.3 | 105 |
| | | 37.5 | 6/6 | −1.5 | 14.7/9.3 | 158 |
| | | 25 | 6/6 | − .9 | 14.0/9.3 | 150 |
| | | 16.5 | 6/6 | − .7 | 13.3/9.3 | 143 |
| | | 62.5 | 4/6 | −2.0 | 10.5/8.9 | 117 |
| | | 37.5 | 4/6 | −1.7 | 19.5/8.9 | 219 |
| | | 25 | 5/6 | − .9 | 18.0/8.9 | 202 |
| | | 16.5 | 6/6 | − .3 | 14.2/8.9 | 159 |
| —CH₂—C₆H₄—p-NO₂ | (β) | 200 | 6/6 | −5.0 | 11.8/11.2 | 105 |
| | | 100 | 6/6 | −3.6 | 12.7/11.2 | 113 |
| —CH₂—C₆H₄—p-NO₂ | (α) | 200 | 5/6 | −3.2 | 10.8/10.7 | 100 |
| | | 100 | 6/6 | −3.3 | 10.8/10.7 | 100 |

The synthesis of 3a, 3b, 3c and 7a, 7b, 7c are illustrative of the generalized process which is conducted optimally at room temperature and atmospheric pressure and required equimolar quantities of the reactants for the substitution reaction. Of course, it is well known that additional amounts of selenium containing reactant may be utilized in special cases to drive the reaction to the right and effect completion thereof.

From the data [J. Med. Chem., 17, 263 (1974)] it is shown that 6-(1-methyl-4-nitroimidazol-5-yl)selenoguanosine is more active (T/C of 255 at 50-mg/kg dose with 6/6 survivors) than 6-selenoguanosine (SeGR). The same trend is observed for the corresponding 2'-deoxy- -derivatives (see Table I above).

PRIOR ART

Townsend and Milne, "Synthesis of the Selenium Congener of the Naturally Occurring Nucleoside Guanosine, 6-Selenoguanosine," *Journal of Heterocyclic Chemistry*, 7, 753 (1970).

Milne and Townsend, "The Synthesis and Chemical Reactivity of 6-Selenoguanosine and Certain Related Derivatives," *Journal of Heterocyclic Chemistry*, 8, 379 (1971).

Milne and Townsend, "The Synthesis of α- and β-2'-Deoxyselenoguanosine," *Biochim. Biophys. Acta*, 269 (1972) 344–346.

Milne and Townsend, "Synthesis and Antitumor Activity of α- and β-2'-Deoxy-6-selenoguanosine and Certain Related Derivatives," *Journal of Medicinal Chemistry*, 17, 263 (1974).

In the present specification and claims, the term "lower alkyl" is defined to mean a straight or branched carbon chain of 1-6 carbon atoms.

PREPARATION OF STARTING MATERIALS (EXAMPLE 1)

EXAMPLE 1-A

Treatment of 2-acetamido-6-chloro-9-(2-deoxy-3-5-di-0-p-toluoyl-β-D- erythro-pentofuranosyl)purine with sodium hydrogen selenide in methanol at reflux temperature for 1 hour under a nitrogen atmosphere effected a nucleophilic displacement of the 6-chloro group as evidenced by thin layer chromatography (tlc) and ultraviolet (uv) spectrum. The protecting groups were then removed with sodium methoxide in methanol at reflux temperature (45 min. under a nitrogen atmosphere). The resulting residue was recrystallized from water to furnish a bright yellow crystalline nucleoside (58%) which was characterized as β-2'-deoxyselenoguanosine (4 ante); m.p. softens at 180° C with decompn at 186° C; ultraviolet $\lambda_{max}^{pH\ 1}$=265 nm ($\epsilon_{max}$ = 6260) and 368 nm ($\epsilon_{max}$ = 18 640); $\lambda_{max}^{methanol}$ = 366 nm ($\epsilon_{max}$ = 22 580); $\lambda_{max}^{pH\ 11}$=254 nm ($\epsilon_{max}$ = 13 650) and 330 nm ($\epsilon_{max}$ = 19 200); PMR ([$^2$H$_6$]dimethyl sulfoxide) sharp singlet at δ8.3 (C-8 proton), a singlet at δ6.8 (exocyclic amino group) a triplet centered at δ6.20 (pk. wd. 14 Hz) (anomeric proton) and the characteristic pattern usually observed for the remaining protons of a 2'-deoxyribofuranose moiety

EXAMPLE 1-B

In the manner of Example 1-A, a similar procedure using 2-acetamido-6-chloro-9-(2-deoxy-3,5-di-0-p-toluoyl-α-D-erythropentofuranosyl)purine furnished a 29% yield of α-2'-deoxyselenoguanosine (2 ante); m.p. 203°–204° C decompn; ultraviolet $\lambda_{max}^{pH\ 1}$=269 nm ($\epsilon_{max}$ = 6260) and 372 nm ($\epsilon_{max}$=21 000); $\lambda_{max}^{methanol}$=261 nm ($\epsilon_{max}$ = 7290) and 365 nm ($\epsilon_{max}$ = 20 210); $\lambda_{max}^{pH\ 11}$=253 nm ($\epsilon_{max}$=13 900) and 330 nm ($\epsilon_{max}$ = 19 310); PMR ([$^2$H]dimethyl sulfoxide) revealed a sharp singlet at δ8.3 (C-8 proton), a singlet at δ6.9 (exocyclic amino group) and a quartet centered at δ6.2 (pk. wd. 10.5 Hz) (anomeric proton) and the characteristic pattern usually observed for the remaining protons of a 2'-deoxyribofuranose moiety. These data were found to be very similar to the data observed for the β-anomer except for the quartet at δ6.2 instead of a triplet which is characteristic for the anomeric proton of an α-2-deoxyribofuranoside.

PREPARATION OF SUBJECT COMPOUNDS EXAMPLES 2–4

EXAMPLE 2-A

2-Amino-6-methylseleno-9-(2-deoxy-β-D-erythropentofuranosyl)purine (7a). To 500 mg (0.0015 mol) of 4 in 25 ml of MeOH containing 100 mg of NaOCH$_3$ was added 250 mg of methyl iodide. The solution was stirred at room temperature for 10 min. and evaporated in vacuo to a foam which was dissolved in 50 ml of MeOH containing 15 ml of J. T. Baker silica gel. The mixture was evaporated to dryness in vacuo and the resulting solid was placed on the top of a nylon dry column (3.75 × 24.5 cm) packed with Baker silica gel + 0.4% of a phosphor. The column was eluted with EtOAc-MeOH (8:1); the uv-absorbing fractions containing nucleoside material were determined by tlc and evaporated in vacuo to afford a residue which was dissolved in 20 ml of H$_2$O and lyophylized. The solid was then placed in a Soxhlet extraction thimble and extracted with diethyl ether (150 ml) at reflux temperature for 48 hr. The ether solution was evaporated to dryness in vacuo, the white solid was dissolved in EtOAc (5 ml), and sufficient cyclohexane was then added to produce a permanent cloud point at the boiling point of the mixture. The solution was allowed to stand at 5° for 18 hr.; the white solid was collected by filtration, washed with 10 ml of cyclohexane, and dried at room temperature for 24 hr. in vacuo to yield 250 mg of product (48%); mp slowly softens to a glass > 70°; uv $\lambda_{max}$ (pH 1) 336 nm ($\epsilon$ 13 600); uv $\lambda_{max}$ (MeOH) 312 nm ($\epsilon$ 14 400); uv $\lambda_{max}$ (pH 11) 316 nm ($\epsilon$ 14 400).

Anal. (C$_{11}$N$_{15}$N$_5$O$_3$Se·0.5H$_2$O) (verified by pmr spectrum) C,H,N.

EXAMPLE 2-B

2-Amino-6-methylseleno-9-(2-deoxy-α-D-erythropentofuranosyl)purine (3a). The procedure was the same as that used for the synthesis of 7a except that 500 mg (0.0015 mol) of 2 was used and the yield from the EtOAc-cyclohexane mixture was 200 mg (39%) of product, mp 167°–170°. For analysis the sample was dried in vacuo over Drierite for 1 hr. at the temperature of refluxing toluene: mp unchanged; uv $\lambda_{max}$ (pH 1) 334 nm ($\epsilon$ 14 400); uv $\lambda_{max}$ (MeOH) 313 nm ($\epsilon$ 15 800); uv $\lambda_{max}$ (pH 11) 316 nm ($\epsilon$ 15 500).

Anal. (C$_{11}$H$_{15}$N$_5$O$_3$Se) C,H,N.

EXAMPLE 3-A

2-Amino-6-p-nitrobenzylseleno-9-(2-deoxy-β-D-erythro-pentofuranosyl)purine (7b). β-2'-Deoxy-6-selenoguanosine (4, 1.0 g, 0.003 mol) was added, with stirring, to 50 ml of MeOH containing 200 mg of NaOCH$_3$. To this mixture was added p-nitrobenzyl bromide (650 mg) and the resulting solution was stirred at room temperature for 15 min. The mixture was allowed to stand at 0° for 2 hr.; the solid was collected by filtration, washed with cold (−20°) MeOH (20 ml), and air-dried. The solid was recrystallized from abolute MeOH and then air-dried to yield 900 mg of product (65%), mp 204°–206° with presoftening at ≅200°. A small sample was recrystallized from MeOH and then dried in vacuo over Drierite for 1 hr. at the temperature of refluxing toluene: mp unchanged; uv $\lambda_{max}$ (pH 1) 282 nm ($\epsilon$ 15 700), 324 (15 700); uv $\lambda_{max}$ (MeOH) 313 nm (ε 19 000); 352 (19 300); uv $\lambda_{max}$ (pH 11) 252 nm (ε 15 300), 313 (13 500).

Anal. ($C_{17}H_{18}N_6O_5Se$) C,H,N.

EXAMPLE 3-B

2-Amino-6-p-nitrobenzylseleno-9-(2-deoxy-α-D-erythropentofuranosyl)purine (3b). The procedure was the same as that for 7b except that 800 mg (0.0024 mol) of 2, 160 mg of NaOCH$_3$, and 520 mg of p-nitrobenzyl bromide were used. The yield after recrystallization from MeOH was 950 mg (83%) of 3b, mp 110° with presoftening at 100°. A sample was dried in vacuo over Drierite at the temperature of refluxing EtOH for 2 hr.: mp unchanged.

Anal. ($C_{17}H_{18}N_6O_5Se \cdot 0.5\ H_2O$) (verified by pmr spectrum) C,H,N.

EXAMPLE 4-A

2-Amino-6-(1-methyl-4-nitroimidazol-5-yl)seleno-9-(2-deoxy-β-D-erythro-pentofuranosyl)purine (7c). β-2'-Deoxy-6-selenoguanosine (4, 1.0 g, 0.003 mol) was added to 50 ml of MeOH containing 200 mg of NaOCH$_3$. To this mixture was added 490 mg of 5-chloro-1-methyl-4-nitroimidazole and the solution stirred at room temperature 0.5 hr. After being adjusted to pH 6–7 with glacial HOAc, the resulting solution was evaporated in vacuo to afford an oily residue. The residue was triturated with 50 ml of acetone and evaporated in vacuo to dryness. This residue was triturated with 20 ml of H$_2$O and then MeOH was added to effect a solution at the boiling point of the mixture. This solution was allowed to stand at 5° for 24 hr.; the solid was collected by filtration, washed with 20 ml of ice water, and dried over CaCl$_2$ in vacuo at 100° for 2 hr. to yield 1.0 g (73%) of product; mp softens at 150° with dec 178° (foams up); uv $\lambda_{max}$ (pH 1) 315 nm (ε14 500); uv $\lambda_{max}$ (MeOH) 246 nm (ε14 100), 310 (ε14 400); uv $\lambda_{max}$ (pH 11) 310 nm (ε15 500).

Anal. ($C_{14}H_{16}N_8O_5Se$) C,H,N.

EXAMPLE 4-B

2-Amino-6-(1-methyl-4-nitroimidazol-5-yl)seleno-9-(2-deoxy-α-D-erythro-pentofuranosyl)purine (3c). The procedure was the same as that for 7c except that 800 mg (0.0024 mol) of 2, 160 mg of NaOCH$_3$, and 400 mg of 5-chloro-1-methyl-4-nitroimidazole were used. The product obtained by crystallization from MeOH—H$_2$O was dried over Drierite in vacuo at the temperature of refluxing toluene for 2 hr. to yield 1.0 g (91%) of 3c: mp 148° softens to a glass.

Anal. ($C_{14}H_{16}N_8O_5Se \cdot 0.5\ H_2O$) (verified by pmr spectrum) C,H,N.

I claim:

1. α-2'-deoxy-6-R-selenoguanosine according to the following structural formula

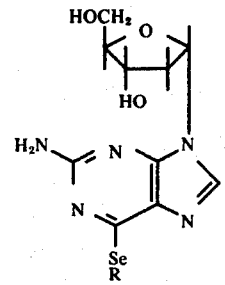

where R is selected from the group consisting of monocyclic aryl, and imidazole.

2. The compound according to claim 1 wherein R is monocyclic aryl.

3. The compound according to claim 1 wherein imidazole is 1-methyl-4-nitroimidazole.

4. The compound according to claim 2 wherein monocyclic aryl is p-nitrobenzyl.

5. β-2'-deoxy-6-R-selenoguanosine according to the following structural formula

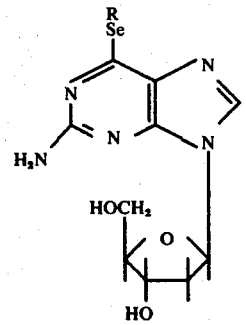

where R is selected from the group consisting of monocyclic aryl, and imidazole.

6. The compound according to claim 5 wherein R is monocyclic aryl.

7. The compound according to claim 5 wherein imidazole is 1-methyl-4-nitroimidazole.

8. The compound according to claim 6 wherein monocyclic is p-nitrobenzyl.

* * * * *

UNITED STATES PATENT OFFICE
CERTIFICATE OF CORRECTION

PATENT NO. : 3,998,806
DATED : December 21, 1976
INVENTOR(S) : Leroy B. Townsend It is certified that error appears in the above-identified patent and that said Letters Patent are hereby corrected as shown below:

Column 1, line 59, "deoxythioguanoisine" should be correctly spelled as --deoxythioguanosine--

Column 5, in Chart III (continued), a double bond is missing. The figure should be

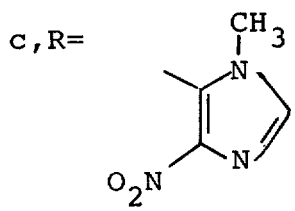

Signed and Sealed this

Eighth Day of March 1977

[SEAL]

Attest:

RUTH C. MASON
Attesting Officer

C. MARSHALL DANN
Commissioner of Patents and Trademarks